Figure 1:
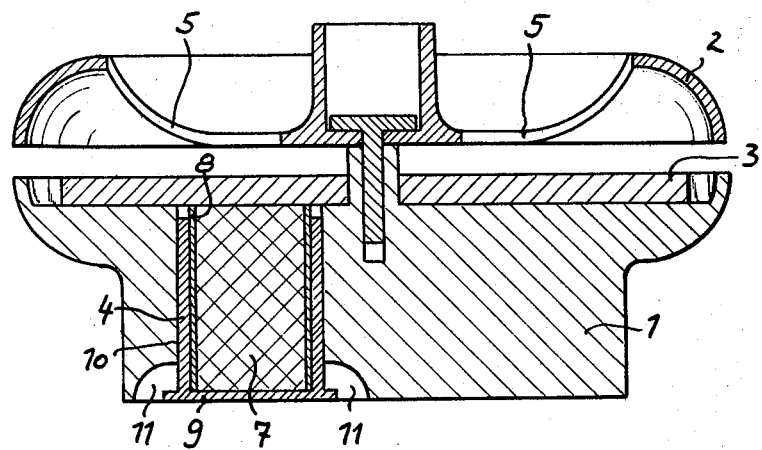

United States Patent [19]

Schimanski et al.

[11] 4,452,393
[45] Jun. 5, 1984

[54] VAPORIZING DEVICE FOR PERFUMES, INSECTICIDES AND/OR OTHER VOLATILE ACTIVE SUBSTANCES

[75] Inventors: Georg Schimanski, Hagen; Fritz von Philipp; Horst Hautmann, both of Neuburg, all of Fed. Rep. of Germany

[73] Assignee: Firma Globol-Werk GmbH, Fed. Rep. of Germany

[21] Appl. No.: 497,066

[22] Filed: May 23, 1983

Related U.S. Application Data

[63] Continuation of Ser. No. 242,221, Mar. 10, 1981, abandoned.

[30] Foreign Application Priority Data

Jun. 20, 1980 [DE] Fed. Rep. of Germany ....... 3023017

[51] Int. Cl.$^3$ ................................................ A61L 9/04
[52] U.S. Cl. ........................................ 239/57; 239/47; 239/56; 239/60
[58] Field of Search ...................... 294/57, 58, 59, 60, 294/56, 47, 44, 45, 49, 309, 313; 116/227, 264, 299

[56] References Cited

U.S. PATENT DOCUMENTS

| | | | |
|---|---|---|---|
| 2,850,321 | 9/1958 | Hoffman | 239/56 |
| 4,166,087 | 8/1979 | Cline et al. | 239/60 |
| 4,293,095 | 10/1981 | Hamilton et al. | 239/47 |

Primary Examiner—James B. Marbert
Attorney, Agent, or Firm—Jacobs & Jacobs

[57] ABSTRACT

Vaporizer device for volatile active substances such as perfumes, insecticides and other volatiles comprising an upper part having openings therein and a lower part with an absorptive slab thereon, the lower part having a capsule filled with absorptive material disposed therein and which may be removed and replaced as desired and means for maintaining the upper and lower parts in operative relationship.

4 Claims, 2 Drawing Figures

VAPORIZING DEVICE FOR PERFUMES, INSECTICIDES AND/OR OTHER VOLATILE ACTIVE SUBSTANCES

This is a continuation of Ser. No. 242,221, filed Mar. 10, 1981, now abandoned.

The present invention relates to a vaporizing device for perfumes, insecticides and/or other volative active substances, the device consisting of a housing which has openings and within which are arranged the active substances, enclosed in a gas-tight capsule, and a support which absorbs the active substances emerging from the opened capsule and active-substance vaporization surfaces facing the housing openings.

One device of this type is known from West German Pat. No. 2,807,424.

In that case the volative active substances are enclosed in liquid form in a gas-tight sleeve and after the opening of the sleeve can run out by means of a mandrel onto an absorptive support so as to be vaporized there.

Such a storing of liquid active substances, however, involves the danger that upon possible, accidental opening of the sleeve the liquid and frequently toxic active substances emerge from the housing, for instance when the latter is in an inclined position, and may be dangerous even to man in this more concentrated form.

The object of the present invention is to make the storing of liquid active-substances and the dispensing thereof to the vaporizer even safer than heretofore by relatively simple means in an apparatus of the general type described above.

This object is achieved by a combination of the following features:

(a) the capsule is filled with absorptive material in which the active substances are stored, and (b) the absorptive material in the capsule is arranged so that it can be brought into contact with the support which absorbs the active substances in such a manner that the active substances stored in the capsule are gradually absorbed by the support.

In this connection, furthermore, the capacity of the absorptive capsule material should correspond at least approximately to the capacity of the support.

By these measures the liquid active substances are now constantly fed as small particles which are noninjurious to man.

Advantageous further embodiments for carrying out the object described above are described in detail hereinafter.

Figure 2:
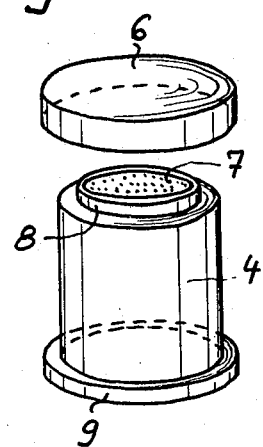

An illustrative embodiment of the invention is shown in the drawing in which:

FIG. 1 shows in a longitudinal section a vaporizer device for perfumes, insecticides and/or other volatile active substances according to the invention, and FIG. 2 is a perspective disassembled view showing details thereof.

The new vaporizing device consists of a bowl-shaped lower part 1 and a hood-shaped upper part 2 which can be attached to the former, the two parts being of circular cross-section and each being made of a single piece of plastic. A support 3 of absorptive cellular material is arranged as a circular ring between the two parts 1 and 2, countersunk in a recess in the upper surface of lower part 1, and a nondeformable capsule 4 which stores the vaporizable active substances.

Openings 5, which may be formed so that they can be closed, are provided in upper part 2 and may be of arcuate shape as shown in FIG. 1.

The capsule 4, shown in detail in FIG. 2, is essentially of pot shape, the mouth of which can be removably closed by a lid 6. The capsule 4 is filled with a core 7 of absorptive cellular material within which the entire active substance is absorbed and stored.

The core 7 is surrounded by a sleeve 8 of plastic foil which is open at its top end.

A flange 9 of greater diameter than the capsule forms a hand grip on the bottom of the capsule.

Within the lower part 1 of the housing there is provided a capsule insertion opening 10 which is open towards the bottom and into which the capsule 4, after removal of its lid 6, is inserted and held in position by friction in such manner that the free end of the cellular core 7 rests in tightly sealing manner against the underside of the plate-shaped support 3 so as to be able to absorb gradually the active substance contained in the capsule 4 depending on the degree of vaporization of the active material.

In the bottom of the lower part 1 there are furthermore provided two finger engagement recesses 11 in order to be able to grasp the capsule more conveniently for removal and replacement. The upper part 2 has a central upstanding hollow portion with a central opening in its base through which the stem of a T-shaped member passes into a hollow boss rising from lower part 1, the top of the T resting normally on the bottom of the upstanding hollow portion.

For the optional delaying of the passage of the active substance from the capsule 4 into the support 3, the capsule 4 can also be so dimensioned that it can be moved to a greater or lesser extent away from the support 3.

In order to obtain the longest lasting, constant vaporization of active substances, the device can also be constructed in such a manner that the free end surface of the capsule core 7 can be brought into contact a part of the wall of the support.

The invention comprises the new individual and combined features disclosed in the specification and/or drawing, which features may be modified as to size, material and relative positions to one another.

We claim:

1. A vaporizing device for perfumes, insecticides and other volatile active substances consisting of a housing having a bowl-shaped lower part, a hood-shaped upper part, and a retention member having a head portion and a stem portion perpendicular thereto, the lower part having a central hollow upstanding boss and the upper surface of the lower part being recessed, a disc-shaped support of absorptive cellular material countersunk in the recess of the lower housing part and of less diameter than the countersink and through which support said boss extends centrally, the hood-shaped upper part having a central upstanding hollow portion with a central opening in its base on which base the head of said retention member rests and from which said stem passes through said opening and through said boss into an opening in the lower part but short of engagement with the bottom of said opening to leave a space therein, the upper housing part having closable arcuate openings radially outwardly of the central upstanding hollow portion, a non-deformable capsule in a capsule-receiving opening in said lower bowl-shaped housing part filled with a removable core of absorptive cellular material for absorption and storage of the active substance inserted in the lower housing portion and having an enlarged flanged base terminating flush with the lowermost surface of the lower housing portion and provided with a closure lid when the capsule is outside the housing but from which capsule the lid is removed prior to insertion in the lower housing part, and finger engagement recesses adjacent the enlarged base for holding the capsule during removal and replacement of the core within the capsule, the core of the absorptive cellular material and the non-deformable capsule being disposed non-centrally of the lower housing part and the housing parts being movable toward and from each other relatively.

2. A vaporizing device according to claim 1, wherein the absorptive capacity of the capsule is substantially equal to the absorptive capacity of the disc-shaped support.

3. A vaporizing device according to claim 1, wherein the core is surrounded by a sleeve of plastic foil.

4. A vaporizing device according to claim 1 wherein the capsule and support are dimensioned for relative movement toward and from each other dependent on the degree of volatility of the active substance and its rate of vaporization.

* * * * *